United States Patent [19]

Kwasman

[11] Patent Number: 5,067,806

[45] Date of Patent: Nov. 26, 1991

[54] QUICK SCREENING FOR SCOTOPIC SENSITIVITY SYNDROME

[75] Inventor: Alan Kwasman, 2844 Taurus, Riverside, Calif. 92503

[73] Assignee: Alan Kwasman, Riverside, Calif.

[21] Appl. No.: 376,553

[22] Filed: Jul. 7, 1989

[51] Int. Cl.$^5$ .............................................. A61B 3/02
[52] U.S. Cl. ................................. 351/233; 351/239; 351/243
[58] Field of Search ............... 351/239, 233, 234, 235, 351/242, 243, 246

[56] References Cited

U.S. PATENT DOCUMENTS 4,293,200 10/1981 Dobson et al. ..................... 351/239
4,526,452 7/1985 Hirsch ................................ 351/243

Primary Examiner—Rodney B. Bovernick

[57] ABSTRACT

A device permitting the rapid determination of scotopic sensitivity syndrome comprised of small cards with colored filters on visual test patterns. The filter's frequencies correspond to the receptor frequencies of the cones in the retina and their combinations.

4 Claims, 1 Drawing Sheet

QUICK SCREENING FOR SCOTOPIC SENSITIVITY SYNDROME

BACKGROUND OF INVENTION

Irlen (see appendix) has discovered empirically that a small percentage of the population can read better using colored lenses. Her findings were confirmed by Adler and Atwood (see appendix) who showed that Irlen lenses improved length of sustained reading and decreased headaches. Possible explanations for this include a lack of visual yellow, a pigment found in the fovea which absorbs blue light. Blue light does not affect fine visual resolution and may create destructive chromatic aberration. Also, color vision depends on the comparison of outputs of cones. Another explanation is that the output of the cones may be misconnected as Galaburda (see appendix) has shown anatomic differences in the brains of dyslexics.

DESCRIPTION OF INVENTION

The invention makes use of seven 3"×5" cards consisting of a visual pattern and a colored filter. The filters are chosen to reflect the spectral sensitivity of the cones and their combinations. I shall call the short, middle, and long wavelength sensitive cones the blue, green, and red cones respectively. There is also one card without a filter.

A detailed description of the operation of the invention will be made in the following paragraphs and in reference to the accompanying drawings.

DESCRIPTION OF PREFERRED EMBODIMENTS

Figures 1, 2:
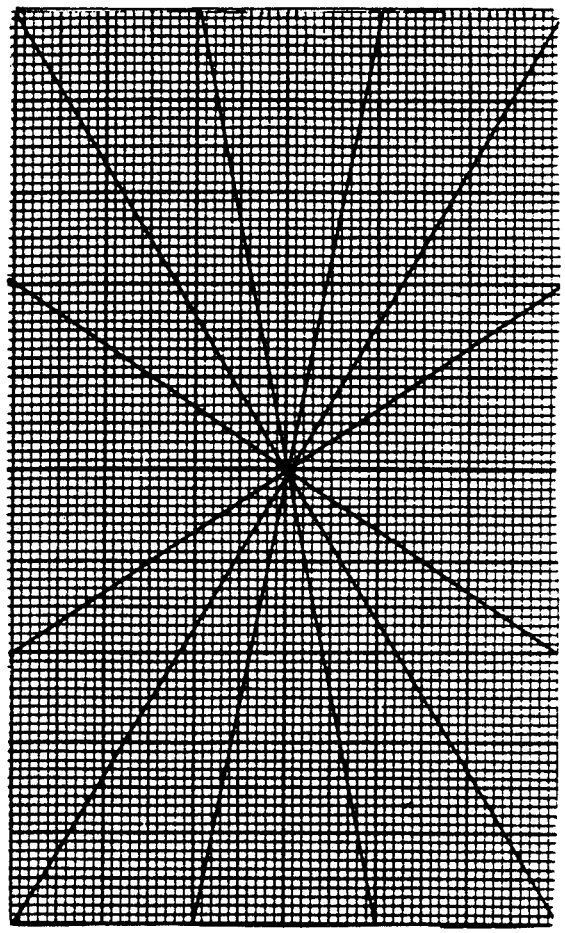
FIG. 1 is a picture of the test pattern (see appendix) used with the filters. The filter is attached to the test pattern.
FIG. 2 is a picture of an alternative test pattern drawn by the author.

The seven cards containing seven filters obtained from Lee Colortran, Inc. (see appendix) consisting of #164 flame red, #196 true blue, #124 dark green, #179 chrome orange, #116 blue-green, #137 special lavendar. These filters were chosen as flame red only stimulates the red cone, true blue was chosen to only stimulate the blue cone, dark green for the green cone, chrome orange for the green and red, blue-green for the blue and green cones, and special lavender to stimulate only the blue and red cones. They are placed over one of the test patterns. Any test pattern may be used. The test pattern which is used is not critical.

The operation of the invention is as follows: two different filtered cards with the same test patterns are shown to the patient by the examiner. The patient is asked which one is clearer. Then whichever one is clearer is kept and compared to the following card, and so on. The last card always given is the one without a filter. The patient is then asked if the filtered image is clearer than the unfiltered. The patient who sees a filtered image better than the unfiltered is referred for further testing by an optometrist familiar with this syndrome. If the unfiltered image is clearer the patient does not have scotopic sensitivity syndrome. Colored filters are not a substitute for reading lessons, educational examination, or physical examination by a medical doctor.

The device is simple and can be operated by relatively unskilled individuals after very little training. It would permit the rapid screening for patients with scotopic sensitivity syndrome.

APPENDIX

1. Irlen, Helen; Irlen Institute for Perceptual and Learning Disabilities, 4425 Atlantic Avenue, Suite A, Long Beach, Calif. 90807.
2. Adler, L. and Atwood M.; Poor Readers: What Do They Really See on the Page? A Study of a Major Cause of Dyslexia; East San Gabriel Valley Regional Occupational Program, 1024 West Workman Avenue, West Covina, Calif. 91790.
3. Galaburda, A M, Kemper T L. Cytoarchitectonic abnormalities in developmental dyslexia: a case study. Ann Neurol 1979; 6: 94–100.
4. Column IV of the Edwin Smith Surgical Papyrus from Breasted, James Henry, The Edwin Smith Surgical Papyrus, 2 volumes, The University of Chicago Press, Chicago, 1930 (as quoted by Kandel, E. and Schwartz, J. in Principles of Neural Science, Second Edition, Elsevier, 1985).
5. Lee Colortran, Inc., 1015 Chestnut Street, Burbank, Calif. 91506-9983.

What is claimed is as follows:

1. A device for determining scotopic sensitivity syndrome consisting of seven cards with a visual test pattern, six of the cards are covered with different colored filters corresponding to frequencies which excite one or two of the color receptors of the eye (cones) at the same time, and one of said cards having no filter; wherein the examiner may determine if a patient has scotopic sensitivity syndrome.

2. The device for determining scotopic sensitivity syndrome as set forth in claim 1 wherein said filters have a non-gloss finish.

3. The device of claim 1 for determining scotopic sensitivity syndrome wherein the visual test pattern is that of FIG. 1.

4. The device of claim 1 for determining scotopic sensitivity syndrome wherein the visual test pattern is that of FIG. 2.

* * * * *